(12) United States Patent
Shalayev et al.

(10) Patent No.: US 10,426,550 B2
(45) Date of Patent: Oct. 1, 2019

(54) ROTATABLE CURVED BIT AND ROBOTIC CUTTING IN ORTHOPAEDIC APPLICATIONS

(71) Applicant: THINK SURGICAL, INC., Fremont, CA (US)

(72) Inventors: Stan Shalayev, Fremont, CA (US); Nathan A. Netravali, Palo Alto, CA (US); In K. Mun, Fremont, CA (US)

(73) Assignee: Think Surgical, Inc., Fremont, CA (US)

( * ) Notice: Subject to any disclaimer, the term of this patent is extended or adjusted under 35 U.S.C. 154(b) by 372 days.

(21) Appl. No.: 15/302,143

(22) PCT Filed: Mar. 31, 2015

(86) PCT No.: PCT/US2015/023655
§ 371 (c)(1),
(2) Date: Oct. 5, 2016

(87) PCT Pub. No.: WO2015/157037
PCT Pub. Date: Oct. 15, 2015

(65) Prior Publication Data
US 2017/0202620 A1 Jul. 20, 2017

Related U.S. Application Data

(60) Provisional application No. 61/978,682, filed on Apr. 11, 2014.

(51) Int. Cl.
*A61B 34/10* (2016.01)
*A61B 17/56* (2006.01)
(Continued)

(52) U.S. Cl.
CPC .......... *A61B 34/10* (2016.02); *A61B 17/1604* (2013.01); *A61B 17/1617* (2013.01);
(Continued)

(58) Field of Classification Search
CPC .. A61B 34/10; A61B 17/1642; A61B 17/1637
See application file for complete search history.

(56) References Cited

U.S. PATENT DOCUMENTS

| 6,430,434 B1 | 8/2002 | Mittelstadt |
| 2006/0122616 A1 | 6/2006 | Bennett et al. |

(Continued)

FOREIGN PATENT DOCUMENTS

WO  2014045119 A2  3/2014

OTHER PUBLICATIONS

Supplementary European Search Report dated Nov. 23, 2017 for European Application No. 15776415 fled Mar. 31, 2015.

*Primary Examiner* — Andrew Yang
(74) *Attorney, Agent, or Firm* — Avery N. Goldstein; Blue Filament Law PLLC (57) ABSTRACT

A process for creating a curved contour on or within a bone is provided, where the process includes positioning a bone of a patient in a fixed position in a coordinate system, generating scan data of the bone, creating a three-dimensional surface model of the bone based on the scan data, generating a cutting program to modify a surface of the bone based on the three-dimensional surface model and a prosthesis having a bone interface shape that is complementary to the curved contour, and modifying the bone with one or more curved blades or a curved drill bit that is robotically driven and positioned with the cutting program to form the curved contour. A system for creating a curved congruent contour on or within a bone for mounting a prosthesis is also described.

14 Claims, 8 Drawing Sheets

(51) Int. Cl.
*A61B 17/16* (2006.01)
*A61B 34/30* (2016.01)
*A61B 17/17* (2006.01)
*A61B 90/00* (2016.01)

(52) U.S. Cl.
CPC .......... *A61B 17/1633* (2013.01); *A61B 17/17* (2013.01); *A61B 17/56* (2013.01); *A61B 34/30* (2016.02); *A61B 2017/1602* (2013.01); *A61B 2017/564* (2013.01); *A61B 2034/102* (2016.02); *A61B 2034/105* (2016.02); *A61B 2090/363* (2016.02)

(56) References Cited

U.S. PATENT DOCUMENTS

| | | | |
|---|---|---|---|
| 2011/0257653 A1* | 10/2011 | Hughes | A61B 34/10 606/79 |
| 2012/0071893 A1 | 3/2012 | Smith et al. | |
| 2012/0323244 A1 | 12/2012 | Cheal et al. | |
| 2013/0035696 A1 | 2/2013 | Qutub | |
| 2014/0005997 A1 | 1/2014 | Park et al. | |
| 2014/0012267 A1 | 1/2014 | Sikora et al. | |

* cited by examiner

ROTATABLE CURVED BIT AND ROBOTIC CUTTING IN ORTHOPAEDIC APPLICATIONS

RELATED APPLICATIONS

This application claims priority benefit of U.S. Provisional Application Ser. No. 61/978,682 filed Apr. 11, 2014; the contents of which are hereby incorporated by reference.

FIELD OF THE INVENTION

This invention relates in general to orthopaedic procedures, and in particular to the creation of exact curved surfaces within, or on bones that replicates the curved surfaces of implants through resort to curved blades and drill bits with precise robotic control.

BACKGROUND OF THE INVENTION

Throughout a subject's lifetime, bones and joints become damaged and worn through normal use and traumatic events. This degradation of the joints involving the articular cartilage and subchondral bone is common to degenerative diseases such as arthritis and results in symptoms including joint pain, tenderness, stiffness, and potential locking of the joint.

Joint replacement arthroplasty is an orthopedic procedure in which the arthritic surface of the joint is replaced with a prosthetic component. It is considered the primary form of treatment to relieve joint pain or dysfunction that may limit mobility. During an arthroplasty procedure, the ends of the bone and articular cartilage are resurfaced (i.e., by cutting the bone) to match the backside of the implant. Current implants used in total knee arthroplasty have flat planar surfaces that connect to the patient's bone, because the current tools used for making the cuts are saws, which are only capable of making flat cuts. Typical femoral implants make use of 5 or 6 planar cuts that conform to the round nature of the condyles. However, in order to preserve the maximum amount of bone, a rounded or curved surface that more closely matches the natural geometry of the femoral condyles would be most effective, but accurately creating these rounded surfaces using conventional manual tools is nearly impossible.

The accurate placement and alignment of an implant is a large factor in determining the success of a joint arthroplasty procedure. Even a slight misalignment there may result in poor wear characteristics, reduced functionality, decreased implant longevity, or a combination of these and other complications.

In order to achieve accurate implant placement and alignment, one must accurately position the cutting tool vis-à-vis the bone prior to making any bone cuts. In some methods, a cutting jig may be used to accurately position and orient a cutting tool such as a saw, drill, or reamer. While in other methods, the cuts may be made using a surgical assist device (e.g., a surgical robot) that controls implements such as a saw, cutter, or reamer. When a surgical assist device is used to make the cuts, the position and orientation of the bone must be known precisely in three-dimensional space (and hence vis-à-vis the surgical assist device) to ensure that the cuts are made in the correct location. Conventional methods of determining spatial orientation and location of a bone require bone registration in a three-dimensional space, either using previously placed fiducial markers or by collecting or digitizing the locations of several points or a digitized matrix on the surface of the bone. The process using previously placed fiducial markers requires an additional surgical operation, and the process of digitizing points on the surface of the bone can be time consuming.

The present applicant in PCT/IB2013/002311 entitled, "SYSTEM AND METHOD FOR REGISTRATION IN ORTHOPAEDIC APPLICATIONS", which is incorporated herein by reference; provides more efficient methods for a surgeon to rapidly and accurately determine the spatial orientation and location of a bone during orthopedic surgery.

While there have been many advancements in patient specific and personalized implants and orthopaedic surgery, there still exists a need for processes and surgical tools that provide bone surface contours that afford a precise, congruent and also improved fit for surgical implants. There further exists a need for a more precise fitting implant to improve implant acceptance and integration to the patient's bone.

SUMMARY OF THE INVENTION

A process for creating a curved contour on or within a bone, where the process includes positioning a bone of a patient in a fixed position in a coordinate system, generating scan data of the bone, creating a three-dimensional surface model of the bone based on the scan data, generating a cutting program to modify a surface of the bone based on the three-dimensional surface model and a prosthesis having a bone interface shape that is complementary to the curved contour, and modifying the bone with one or more curved blades or a curved drill bit that is robotically driven and positioned with the cutting program to form the curved contour.

A system for creating a curved congruent contour on or within a bone includes a processor configured to receive patient scan data and to generate a three-dimensional model and a cutting program to modify the surface of the bone based on the three-dimensional surface model and a prosthesis having a bone interface shape complementary to the curved contour, and a machine controlled by the processor and mechanically coupled to at least one curved blade or curved drill bit, the machine robotically driven and positioned with the cutting program to modify the bone to form the curved contour.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

DESCRIPTION OF THE INVENTION

The present invention has utility for the application of curved blades and drill bits with precise robotic control for the creation of exact curved surfaces or other congruent surfaces within or on bones that replicate the curved surfaces or any other non-linear surfaces of implants during orthopaedic procedures. A system and process is provided for a surgeon to rapidly and accurately use curved blades or drills with precise robotic control to create highly accurate curved surfaces on or within bone for joint arthroplasty.

While rotatable curved blades and drill bits have been available and used for ear, nose, and throat (ENT) procedures, such as ethmoidectomy or urcinectomy, these surgical tools have never been applied to orthopaedic surgery. Furthermore, curved blades and drill bits have never been combined with software driven robotic control, and these surgical tools have been primarily designed for use with hand tools, which allows them to be used in the curved cavities present in ENT surgeries. The application of curved blades with precise robotic control in embodiments of the invention allows for rapid creation of exact curved surfaces that replicate the curved surfaces of implants such as those used in total hip and knee arthroplasty, in contrast to current implants used in total knee arthroplasty that have flat planar surfaces, since the current tools used for making the cuts are saws, which are only capable of making flat cuts. Currently, femoral implants make use of 5 or 6 planar cuts that conform to the round nature of the condyles. However, in order to preserve the maximum amount of bone, via bone conservation protocols, a rounded or curved surface that more closely matches the natural geometry of the femoral condyles would be most effective. Accurately creating these rounded surfaces using conventional manual tools is nearly impossible. In embodiments of the invention, the use of curved blades and drills with robotic control allows for the removal of a minimal amount of bone, and creates a matching surface to a curved backside of an implant. Furthermore, embodiments of the invention may be used in any application where curved cuts within bone might be advantageous. For example, embodiments of the inventive process may be universally used to prepare curved trajectories involving any bone drill cuts with the advantage of variable angled cutters, and the ability to precisely match the surgical pre planning and achieve exact trajectories to match the curved surfaces of implants such as total hip arthroplasty femoral components. Additionally, embodiments of the inventive process may be utilized in bone removal techniques by "layers" in which thin layers of bone are removed sequentially to achieve optimal bone preservation.

The precise curved bone surface obtained with embodiments of the invention is advantageous for the allowance of potential bone ingrowth interface with the preservation of a "healthy" pool of osteoblastic cells with differentiative capabilities that can be triggered via "non impacted irritative processes of non thermal necrotic nature" due to the improved cutting of these surfaces when compared with other cutting techniques, and utilizing "bone layering" techniques to decrease the temperature gradient at the cutting site. Furthermore, compared to current robotic milling techniques, the use of robotic control results in removal of bone tissue in larger blocks instead of milling bone layer by layer and resulting in bone slurry. This would also decrease destabilization of the bony architecture via minimizing disruption of the interfaces between subchondral/cortical/cancellous bone. The larger blocks of bone also present an advantage to be saved for tissue banks or other clinical applications where bone tissue is needed. This justifies the ability to reintroduce patient specific bone tissue for regenerative processes or for pharmaceutical agent scaffold utilization.

Figure 1:
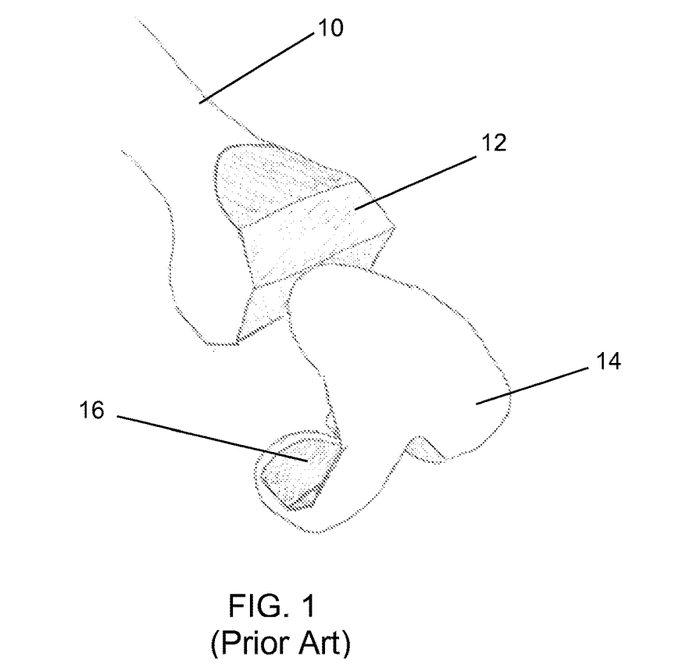
FIG. 1 is a perspective view depicting a traditional femoral total knee arthroplasty (TKA) prosthesis (total knee replacement) with planar cuts and implant-bone interface.

Referring now to the figures, FIG. 1 is a perspective view depicting a traditional femoral total knee arthroplasty (TKA) prosthesis 14 (total knee replacement) with planar cuts 12 in a bone 10 that matches implant-bone interface 16 of the prosthesis 14.

Figure 2:
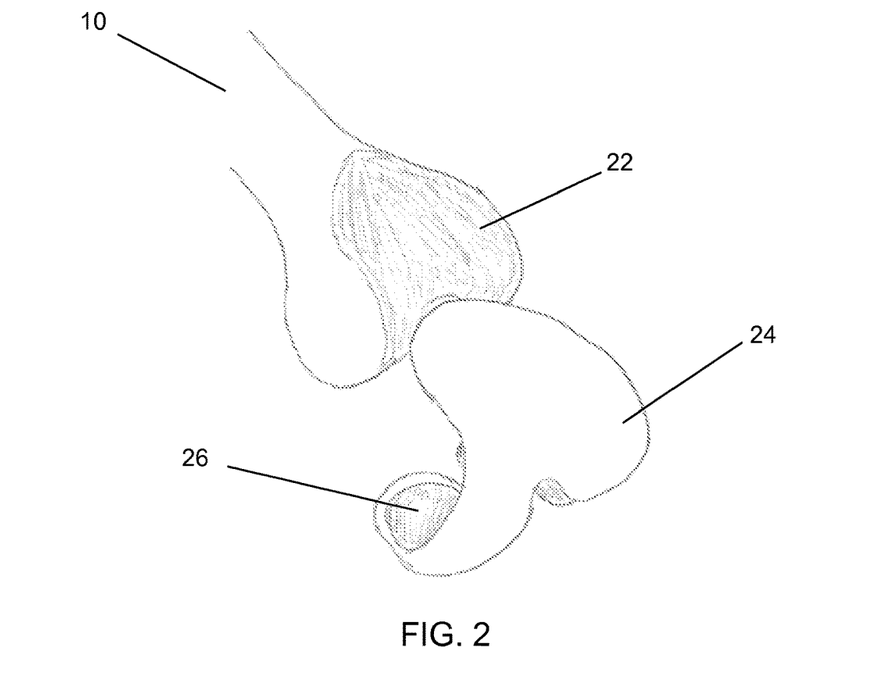
FIG. 2 is a perspective view depicting a femoral total knee arthroplasty (TKA) prosthesis (total knee replacement) with curved surfaces on the backside for which the bone can be prepared using the curved blades and robotic control according to an embodiment of the invention.

FIG. 2 is a perspective view depicting a femoral total knee arthroplasty (TKA) prosthesis 24 (total knee replacement) with curved surfaces 26 on the backside for which the bone 10 may be prepared with a curved contour 22 using the curved blades and robotic control according to an embodiment of the invention.

Figure 3:
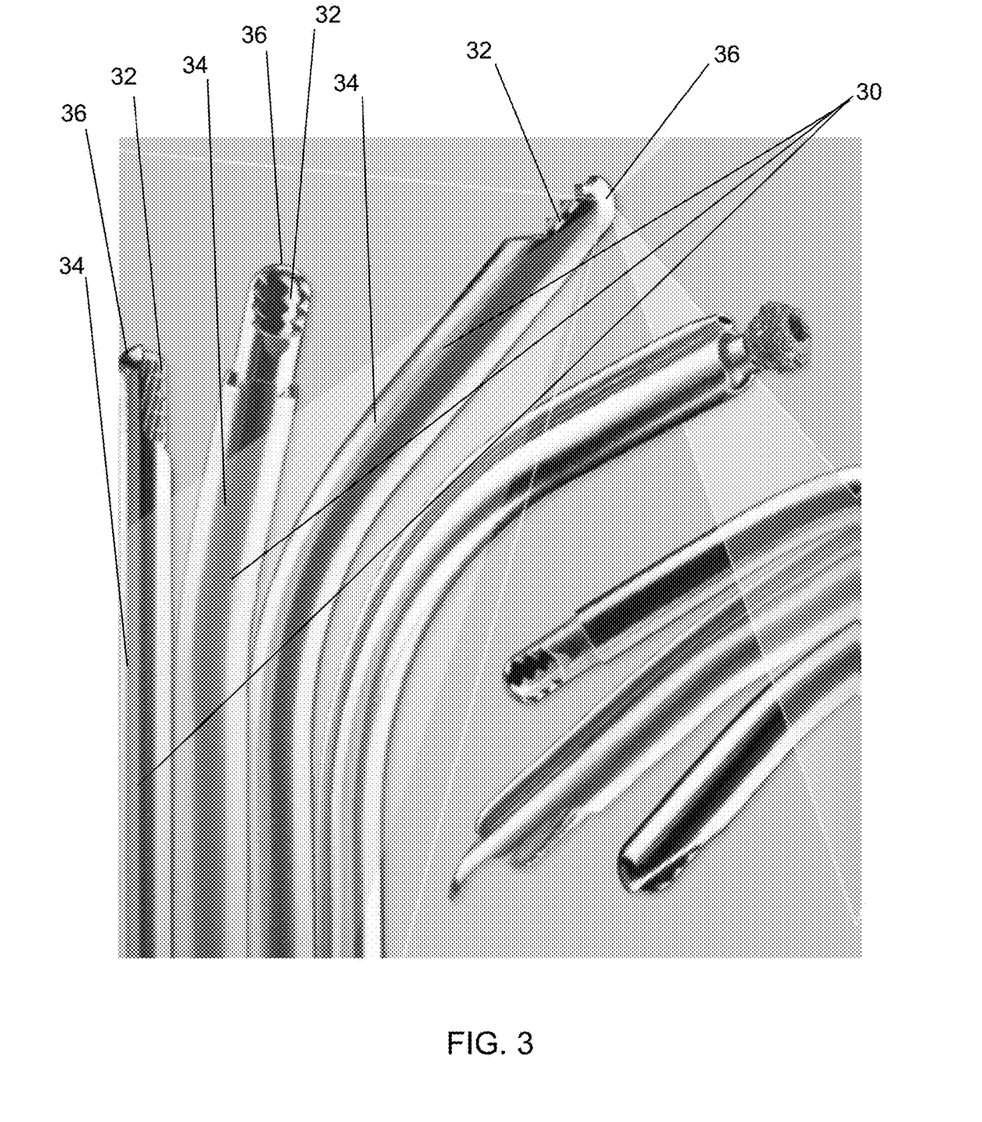
FIG. 3 shows examples of surgical curved blades and drill bits that can be adapted for use with embodiments of the invention.

FIG. 3 shows examples of surgical curved blades and drill bits 30 that can be adapted for use with embodiments of the invention. The curved drill bits 30 may be robotically driven and positioned based on a cutting program to form a curved contour in a bone. Each of the curved drill bits 30 may have a rotatory head 32 extending from a nonlinear shaft 34 and rotating within the nonlinear sheath 36.

In a specific embodiment, a system for creating a three-dimensional model of a patient's bone is provided, the system including a processor configured to receive patient scan data and to transform the patient scan data into a three-dimensional virtual model and create the adjustable model instructions based on the three-dimensional virtual model. A malleable registration guide blank is configured to couple to the adjustable model and to be shaped to fit the adjustable model to form a shaped custom registration guide that is configured to fit to the patient's bone in a unique way.

A system for intraoperatively determining the location of a patient's bone is also provided, the system including a digitizer configured to determine intraoperatively the location of the fiducial markers, and a processor, coupled to the digitizer, and configured to determine the location of the registration guide with respect to the fiducial markers and to determine the location of the patient's bone with respect to the registration guide.

An adjustable registration jig and systems for fitting such registration jigs to a bone using a preoperative planning software is provided. The registration jigs are adjustable such that the registration jigs may be placed on the bone surfaces of specific patients and the settings adjusted such that the registration jigs fit on the bone in a unique manner. The preoperative planning software determines the settings for the adjustable jig such that the jig fits precisely on the bone. The preoperative planning software uses medical images including but not limited to computed tomography (CT), magnetic resonance imaging (MRI), or X-ray scans of patients' bones as input. The scan data may be used to create a three-dimensional model of the bone(s) involved in the procedure using the preoperative planning software.

In a specific embodiment, each bone has a generic adjustable jig that may be placed on the bone and secured to the bone surface by adjusting some settings. The settings on these generic adjustable jigs may be changed to accommodate bones of a variety of sizes. The jigs may be made from polymer, ceramic, metal, or other suitable material, and sterilized, or alternatively jigs may be prefabricated via 3D printing processes with respect to the specific implant of the procedure. The preoperative planning software then determines the appropriate settings for the registration jig such that the jig will securely mate with the bone surface. The adjustable jigs have three or more fiducial markers that may be optical, mechanical, or electro-magnetic. The fiducial markers may be a part of the registration jig or they may be separate modular pieces that attach to the registration jig in a specific location, or that attach directly to the bone through an opening in the jig. The fiducial markers, whose positions relative to the registration jig are known and whose positions relative to the patient bone will be known once the registration jig is placed on the bone and adjusted to its unique position, may then be rapidly located intraoperatively to determine the spatial orientation of the bone in three-dimensions.

In another embodiment, the preoperative planning software generates a three-dimensional model of an adjustable jig that consists of multiple pieces that mate with the surface of the bone. The jigs multiple pieces attach to each other using an adjustable mechanism, such as a rail. The preoperative planning software determines the appropriate settings for the registration jig such that the jig will securely mate with the bone surface. In this embodiment, the registration jig fits on the surface of the bone in a unique manner making use of the specific anatomy of the patient that may include distinguishing features such as worn bone surfaces or osteophytes. The software can determine three or more specific points on the registration jig that may be used to rapidly determine the spatial location and orientation of the adjustable jig. These specific registration points may serve as locations for fiducial markers that can be optical, mechanical, or electro-magnetic. The fiducial markers may be a part of the registration jig or the fiducial markers may be separate modular pieces that attach to the registration jig in a specific location or that attach directly to the bone through an opening in the jig. The fiducial markers, whose positions relative to the registration jig are known and whose positions relative to the patient bone will be known once the registration jig is placed on the bone in its unique position, may then be rapidly located intraoperatively to determine the spatial orientation of the bone in three-dimensions.

In certain embodiments, the preoperative planning software generates instructions for computer-controlled tool paths to machine the patient-specific registration jigs in a tool path data file. The tool path can be provided as input to a CNC mill or other automated machining or rapid prototyping system, and the registration jigs may be machined from polymer, ceramic, metal, or other suitable material, and sterilized. The customized patient specific jigs are spatially registered to the bone surface in three-dimensional space. The parts of the registration jig may be made of varying thickness, but shall be made of a minimum thickness such that the guide can maintain its structural stiffness without deformation. Certain areas of the jig may be made thicker to provide this structural rigidity.

During surgery, once the registration jig is applied to the bone intraoperatively, the jig can be adjusted such that it fits on the bone securely in a unique manner. The jig may be secured to the bone using fixation pins, fasteners, or another process of immobilizing the jig with respect to the bone. The fixation pins may or may not also serve as the fiducial markers. Once the location of the fiducial markers has been determined using a digitizer or other digital location device, the location and orientation of the underlying bone may be determined as there is a unique relationship between the orientation and location of the registration jig and that of the bone when the settings on the registration jig are adjusted according to the preoperative planning software. Prior to beginning the bone cutting, the registration jig may or may not be removed from the bone surface. If the registration jig is removed from the surface of the bone, the fiducial markers preferably remain attached to the bone during bone cutting. These fiducial markers may be used at any point during the surgery to rapidly determine the location and orientation of the bone.

The registration jig may be modular in nature, consisting of multiple pieces. Once the registration jig is adjusted and is secured to the bone, part of the registration jig may be removed from the bone, leaving part of the jig fixed to the bone. The portion of the registration jig that remains fixed to the bone should contain on or within it, fiducial markers that may be used to determine the location and orientation of the registration jig. Once the location and orientation of these fiducial markers is known, the original location of the registration jig may be determined and the location and orientation of the underlying bone may be determined as there is a unique mating between the bone and the registration jig.

The registration jig or guide may be customized to fit the contours of an individual patient bone surface. Depending on the embodiment, the registration guides are automatically planned and generated. The preoperative planning software uses medical images including CT, MRI, or X-ray scans of patients' bones as input. The scan data can be used to create a three-dimensional model of the bone(s) involved in the procedure using the preoperative planning software. The software then generates a three-dimensional model of a registration guide that mates with the surface of the bone. Based on the three-dimensional model, the software generates instructions for computer-controlled tool paths to machine the patient-specific registration guide in a tool path data file. The tool path may be provided as input to a CNC mill or other automated machining or rapid prototyping system, and the registration guides may be machined from polymer, ceramic, metal, or other suitable material, and sterilized. The registration guide may be made of varying thickness, but is often made of a minimum thickness such that the guide can maintain a structural stiffness and bone interface integrity without deformation. Certain areas can be made thicker to provide this structural rigidity.

The generated registration guide fits on the surface of the bone in a unique manner making use of the specific anatomy of the patient that may include distinguishing features such as worn bone surfaces or osteophytes. The software can determine three or more specific points on the registration guide that may be used to rapidly determine the spatial location and orientation of the registration guide. These specific registration points can serve as locations for fiducial markers that can be optical, mechanical, or electro-magnetic. The fiducial markers may be a part of the registration guide or they may be separate modular pieces that attach to the registration guide in a specific location or that attach directly to the bone through an opening in the registration guide. The fiducial markers, whose positions relative to the registration guide are known, and whose positions relative to the patient bone will be known once the registration guide is placed on the bone in its unique position, can then be rapidly located intraoperatively to determine the spatial orientation of the bone in three-dimensions.

During surgery on the subject patient for which the customized guide was formed, once the registration guide is applied to the bone intraoperatively, the guide may be secured to the bone using fixation pins, fasteners, or another process of immobilizing the guide with respect to the bone. The fixation pins may or may not also serve as the fiducial markers. Once the location of the fiducial markers has been determined using a digitizer or other digital locating device, the location and orientation of the underlying bone can be determined as there is a unique mating between the registration guide and the bone. Prior to beginning the bone cutting, the registration guide may or may not be removed from the bone surface. If the registration guide is removed from the surface of the bone, the fiducial markers shall preferably remain attached to the bone during bone cutting. These fiducial markers may be used at any point during the surgery to rapidly determine the location and orientation of the bone.

In a certain embodiment of the customized registration guide, the registration guide may be modular in nature, consisting of multiple pieces. Once the registration guide is secured to the bone, part of the registration guide may be removed from the bone, leaving part of the guide fixed to the bone. The part of the registration guide that remains fixed to the bone should contain on or within it, fiducial markers that may be used to determine the location and orientation of the registration guide. Once the location and orientation of these fiducial markers is known, the original location of the registration guide may be determined and the location and orientation of the underlying bone may be determined as there is a unique mating between the bone and the registration guide.

The determination of the location and the position of a patient's bone in three-dimensional space enables a surgical procedure to be performed on the bone in its known location. For example, this may be particularly useful in robotic-assisted or computer-assisted surgery (e.g., computer navigation). For example, in a joint arthroplasty procedure in the orthopedic surgery field, accurate placement and alignment of an implant is a large factor in determining the success of the procedure. A slight misalignment may result in poor wear characteristics, reduced functionality, and a decreased longevity. Knowing the exact location of the bone in three-dimensional space prior to making any bone cuts enables accurate implant placement and alignment.

For example, a joint arthroplasty procedure in the orthopedic surgery field may be performed knowing the exact location of the bone in three-dimensional space prior to making any bone cuts, thereby enabling accurate implant placement and alignment and improved likelihood of success of the procedure. Another example, an osteotomy procedure in the orthopedic surgery field may be performed knowing the orientation of the bone in three-dimensional space prior to making the bone cuts to increase the accuracy of making the bone cuts and congruent surfaces as desired.

Figure 4:
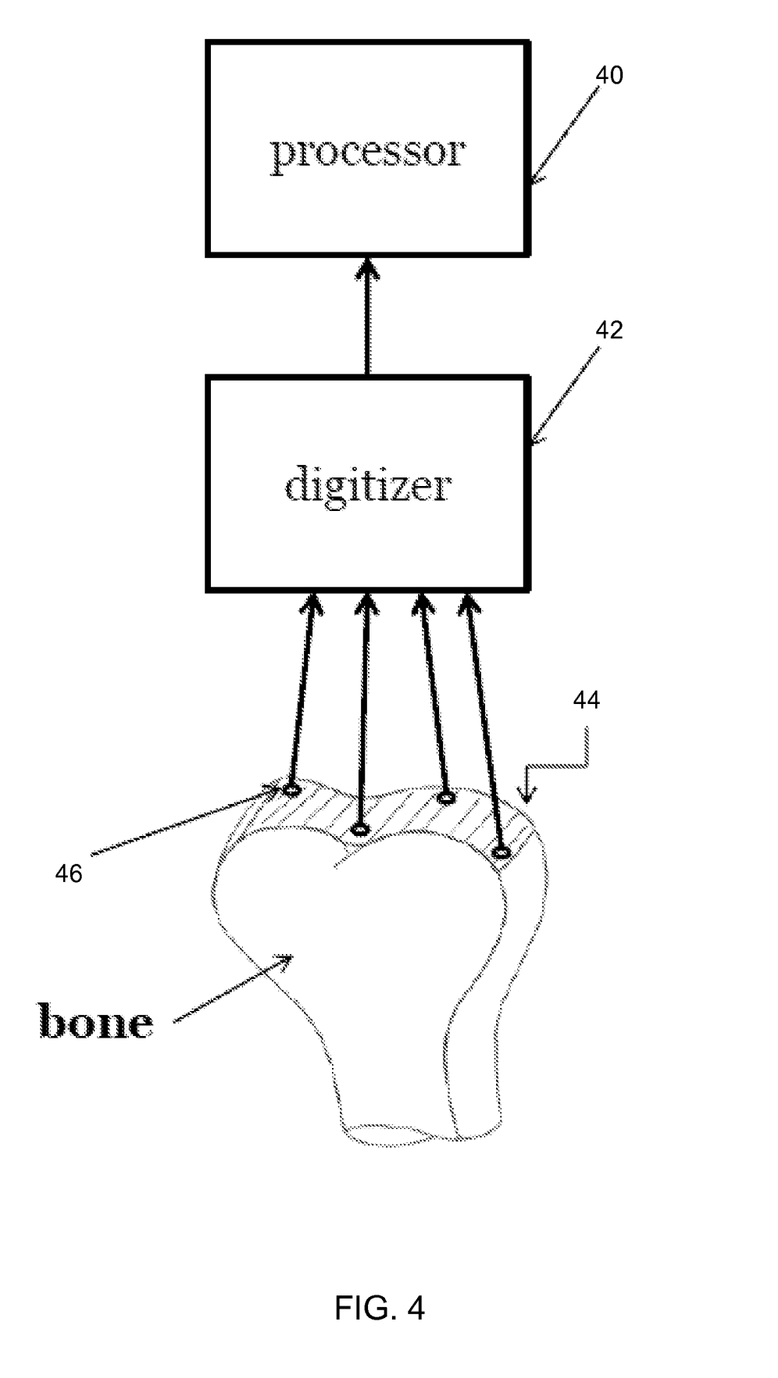
FIG. 4 illustrates a system for intraoperatively determining the location of a patient's bone.

As shown in FIG. 4, a system for intraoperatively determining the location of a patient's bone includes a custom registration guide 44, a digitizer 42 configured to determine intraoperatively the location of the fiducial markers 46; and a processor 40, coupled to the digitizer 42, and configured to determine the location of the registration guide with respect to the fiducial markers and to determine the location of the patient's bone with respect to the registration guide. The system preferably functions to precisely locate the position of a patient's bone in three-dimensional space to enable a surgical procedure to be performed on the bone in its known location. For example, this may be particularly useful in robotic-assisted or computer-assisted surgery (e.g., computer navigation). For example, in joint arthroplasty procedure in the orthopedic surgery field, accurate placement and alignment of an implant is a large factor in determining the success of the procedure. A slight misalignment may result in poor wear characteristics, reduced functionality, decreased longevity, or a combination of these and other complications. Knowing the exact location of the bone in three-dimensional space prior to making any bone cuts enables accurate implant placement and alignment.

Continuing with FIG. 4, the custom registration guide 44 is coupled to the patient's bone. In certain embodiments, the guide 44 is fixed or immobilized with respect to the patient's bone. As described in detail above, the digitizer 42 in some inventive embodiments functions to determine intraoperatively the location of the fiducial markers 46. Once the location of the fiducial markers is known, the processor 40 preferably functions to determine the location of the registration guide 44 with respect to the fiducial markers 46, and to determine the location of the patient's bone with respect to the registration guide 44.

The processor 40 in some inventive embodiments functions to determine the location of the registration guide 44 with respect to the fiducial markers 46 based on the known spatial relationship between the fiducial markers 46 and the registration guide 44, and to determine the location of the patient's bone with respect to the registration guide 44 based on the unique fit and known spatial relationship between the registration guide 44 and the patient's bone. Once the location of the fiducial markers 46 has been determined, the location and orientation of the underlying bone may be determined, as there is a unique mating between the registration guide 44 and the bone, and the position of the fiducial markers 46 with respect to the registration guide 44 is known by the design of the registration guide 44.

Figure 5:
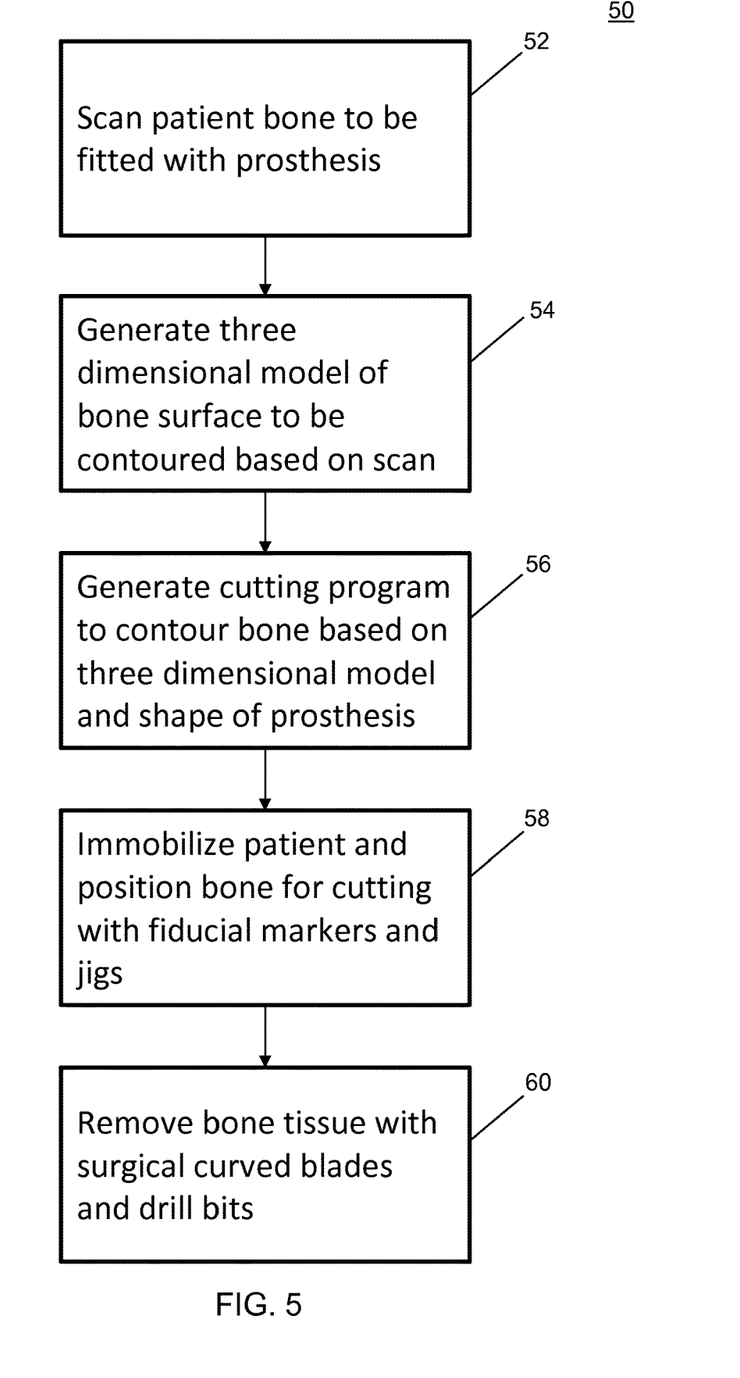
FIG. 5 is a flowchart depicting a process for the use of curved blades and drill bits with precise robotic control for the creation of exact curved surfaces within or on a patient's bones that replicate the curved surfaces of implants according to an embodiment of the invention.

FIG. 5 is a flowchart depicting a process 50 for the use of curved blades and drill bits with precise robotic control for the creation of exact curved surfaces within or on a patient's bones that replicate the curved surfaces of implants according to an embodiment of the invention. The process starts with a scan of the patient's bone to be fitted with a prosthesis (step 52). Based on the scan a three dimensional model of the bone surface to be contoured is generated (step 54). Subsequently, a cutting program to contour the bone based on the three dimensional model and the shape of the bone interface of the prosthesis is generated (step 56). The patient is then immobilized and positioned in a coordinate system for surgery with jigs and fiducial markers fitted to the bone (step 58). Bone tissue is removed with the surgical curved blades and drill bits to produce a required contoured surface to fit the prosthesis (step 60).

Figure 6:
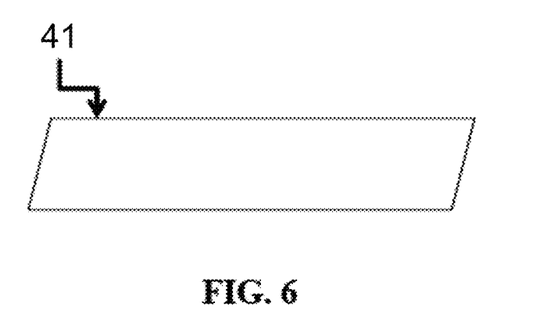
FIG. 6 illustrates a malleable registration guide blank in accordance with embodiments of the invention.
Figure 7A:
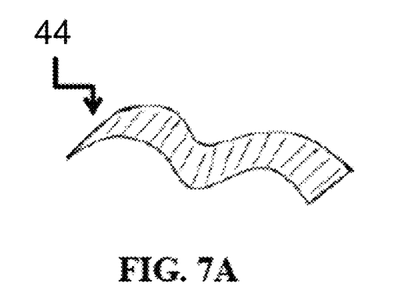
FIGS. 7A and 7B illustrates exemplary malleable registration guides in a shaped configuration in accordance with embodiments of the invention.
Figure 7B:
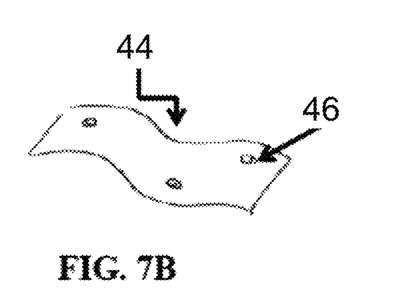

Continuing with FIG. 6 and FIGS. 7A and 7B, a registration guide 44 may be formed from a malleable registration guide blank 41 that is preferably configured to conform to the shape of an adjustable model as described in PCT/IB2013/002311. The blank 41 may be pressed, hammered, or molded onto the outer surface of the adjustable model. For example, the malleable registration guide blank 41 may be a thin malleable sheet of material. For example, the blank 41 may be made of any suitable malleable metal or plastic. The material of the registration guide is preferable sterile and/or sterilizable, and the material may be hammered or pressed permanently into shape without breaking or cracking. In other words, the blank 41 preferable holds the shape of the three dimensional model once it is shaped against the model. In certain embodiments, the material for the blank 41 may be melted or warmed before it is placed onto the model such that it will conform to the model and then cool to hold its shape. In some embodiments, the model may further include vacuum or suction such that the blank 41 may be pulled against the model and shaped. In some embodiments, the malleable material may be heated or cured to increase its material stiffness once it has been shaped against the model. The malleable registration guide blank 41 may alternatively be shaped against the model in any other suitable fashion.

In certain embodiments, the registration guide 44 may be modular in nature, consisting of multiple pieces. The pieces of the registration guide 44 may each be shaped against the model. In some embodiments, the pieces of the registration guide 44 may be fixed or coupled together and then configured to break apart. For example, once the registration guide 44 is secured to the bone, part of the registration guide can be removed from the bone, leaving part of the guide fixed to the bone. The part that remains fixed to the bone preferably contains on or within it, fiducial markers that may be used to determine the location and orientation of the registration guide 44. Once the location and orientation of these fiducial markers 46 is known, the original location of the registration guide can be determined and the location and orientation of the underlying bone can be determined as there is a unique mating between the bone and the registration guide 44.

As shown in FIGS. 7A and 7B the shaped custom registration guide 44 is preferably configured to fit to the patient's bone in a unique way. As shown, the shaped registration guide 44 holds the shape received from the model. The registration guide 44 includes an anatomy-specific inner surface that mates with the bone surface in a unique manner and an external surface, as shown in FIG. 7B, including fiducial markers 46 or distinguishing features that can be used to determine the location of the registration guide 44. The fiducial makers 46 may be optical, mechanical, electromagnetic, or any other suitable markers. The fiducial markers 46 may be a part of the registration guide, or the fiducial markers 46 may be separate modular pieces that attach in a specific location or through an opening in the guide 44. The fiducial markers 46, whose positions relative to the registration guide 44 are known, and whose positions relative to the patient bone will be known once the registration guide 44 is placed on the bone in its unique position, can then be rapidly located intraoperatively to determine the spatial orientation of the bone in three-dimensions. The registration guide 44 and/or fiducial markers 46 may or may not be removed from the patient bone prior to cutting of the bone surface.

In one specific embodiment, the patient's bone may include a proximal tibia. The custom registration guide 44 may be created such that it conforms to the surface of the bone, and reaches over at least three of the four sides of the tibial plateau (anterior, posterior, medial, and lateral), thus ensuring that the guide 44 will fit on the bone in a unique manner. In another specific embodiment, the patient's bone may include the distal femur. The custom registration guide 44 may be created such that it conforms and mates with the femoral joint surface of the patient and nests within the femoral intercondylar notch. In a third specific embodiment, the patient's bone includes the proximal femur for a total hip arthroplasty procedure. The custom registration guide 44 may be created such that it conforms and mates with the femoral joint surface of the patient. The custom registration guide 44 may fit in a conforming manner on the surface of the femoral head and neck in a unique position.

Figure 8:
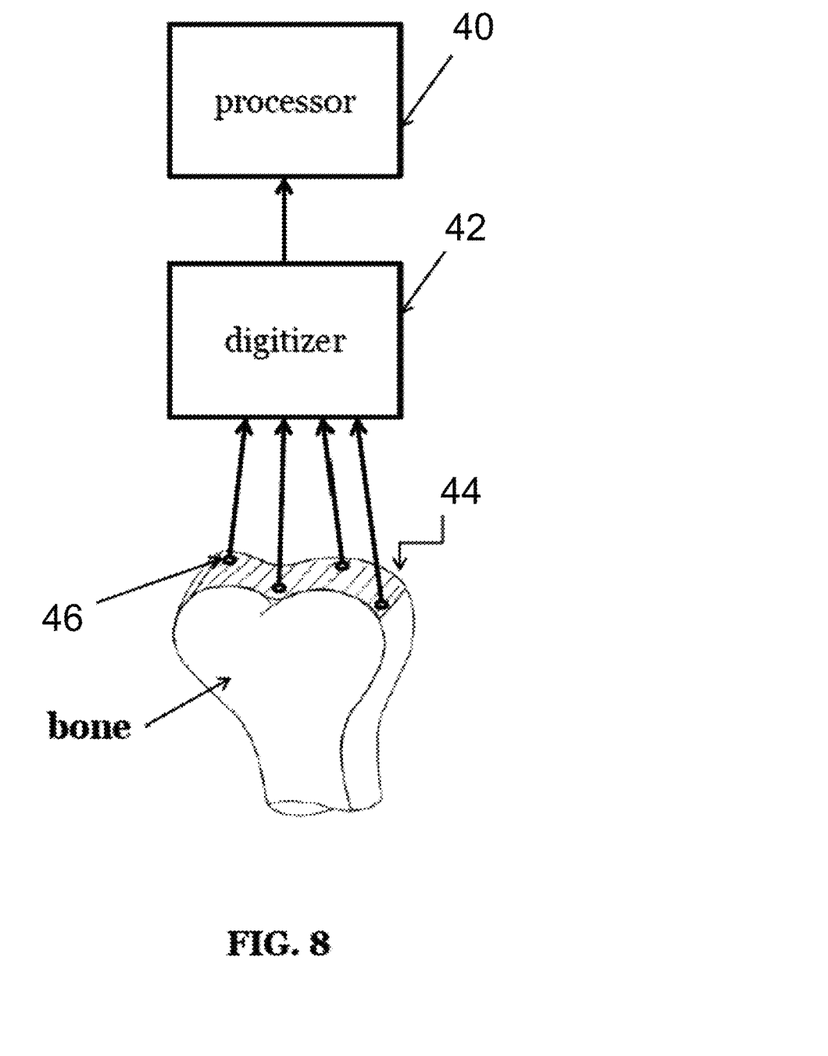
FIG. 8 illustrates an exemplary malleable registration guide in a shaped configuration, as shown in FIG. 7A, fixed to the exemplary patient bone as shown in FIG. 4 according to an embodiment of the invention.

As shown in FIG. 8, an embodiment of a system for intraoperatively determining the location of a patient's bone includes a custom registration guide 44, a digitizer 42 configured to determine intraoperatively the location of the fiducial markers 46; and a processor 40, coupled to the digitizer 42, and configured to determine the location of the registration guide with respect to the fiducial markers and to determine the location of the patient's bone with respect to the registration guide. The system preferably functions to precisely locate the position of a patient's bone in three-dimensional space to enable a surgical procedure to be performed on the bone in its known location. For example, this may be particularly useful in robotic-assisted or computer-assisted surgery (e.g., computer navigation). For example, in joint arthroplasty procedure in the orthopedic surgery field, accurate placement and alignment of an implant is a large factor in determining the success of the procedure. A slight misalignment may result in poor wear characteristics, reduced functionality, and a decreased longevity. Knowing the exact location of the bone in three-dimensional space prior to making any bone cuts enables accurate implant placement and alignment.

As shown in FIG. 8, the custom registration guide 44 is coupled to the patient's bone. In certain embodiments, the guide 44 is fixed or immobilized with respect to the patient's bone. As described in detail above, the digitizer 42 preferably functions to determine intraoperatively the location of the fiducial markers 46. Once the location of the fiducial markers 46 is known, the processor 40 preferably functions to determine the location of the registration guide 44 with respect to the fiducial markers 46, and to determine the location of the patient's bone with respect to the registration guide 44.

The processor 40 preferably functions to determine the location of the registration guide 44 with respect to the fiducial markers 46 based on the known spatial relationship between the fiducial markers 46 and the registration guide 44, and to determine the location of the patient's bone with respect to the registration guide 44 based on the unique fit and known spatial relationship between the registration guide 44 and the patient's bone. Once the location of the fiducial markers 46 has been determined, the location and orientation of the underlying bone can be determined, as there is a unique mating between the registration guide 44 and the bone, and the position of the fiducial markers 46 with respect to the registration guide 44 is known by the design of the registration guide 44.

Figure 9:
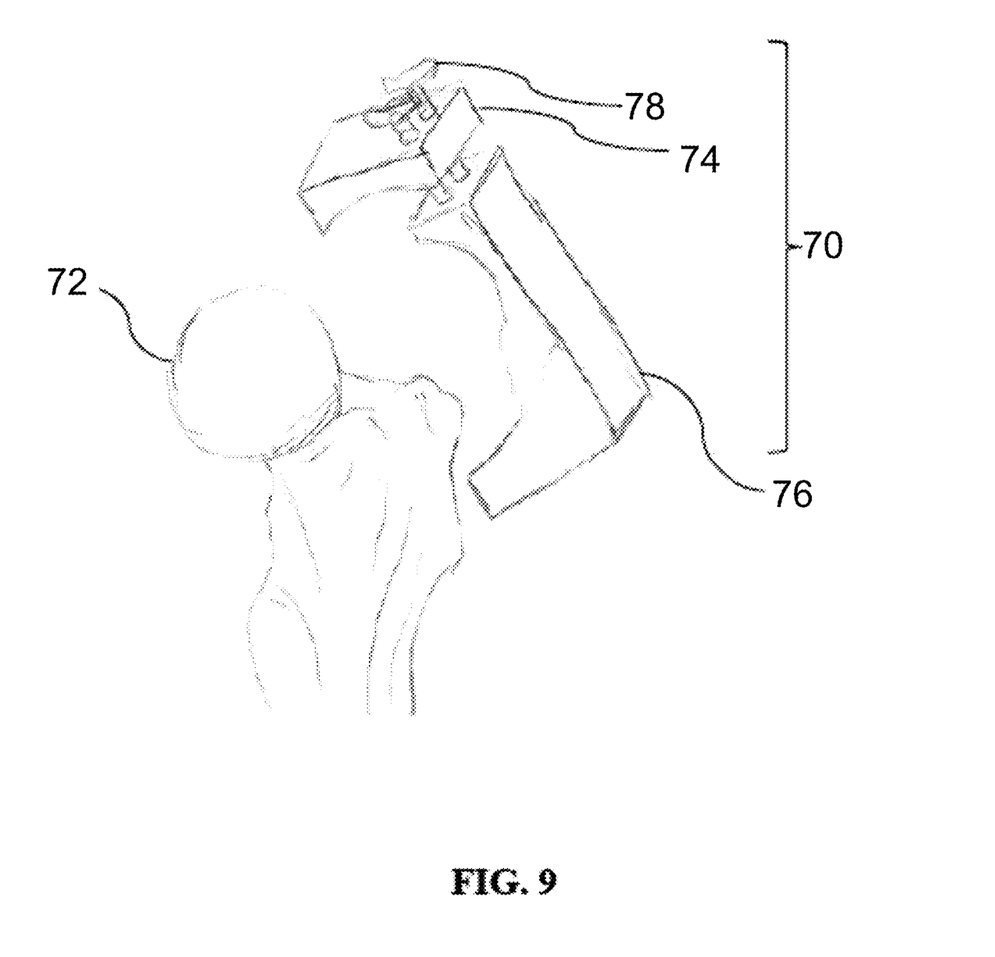
FIG. 9 is a perspective view of a proximal femur with an embodiment of the adjustable registration jig in position on the bone.

FIG. 9 is a perspective view of a proximal femur 72 with an embodiment of the adjustable registration jig 70. The jig 70 is made of two separate upper 74 and lower 76 parts that conform exactly to the surface of the bone and can be adjusted using a mechanism 78, which ensures that the guide fits on the bone 72 securely in a unique manner.

Figure 10:
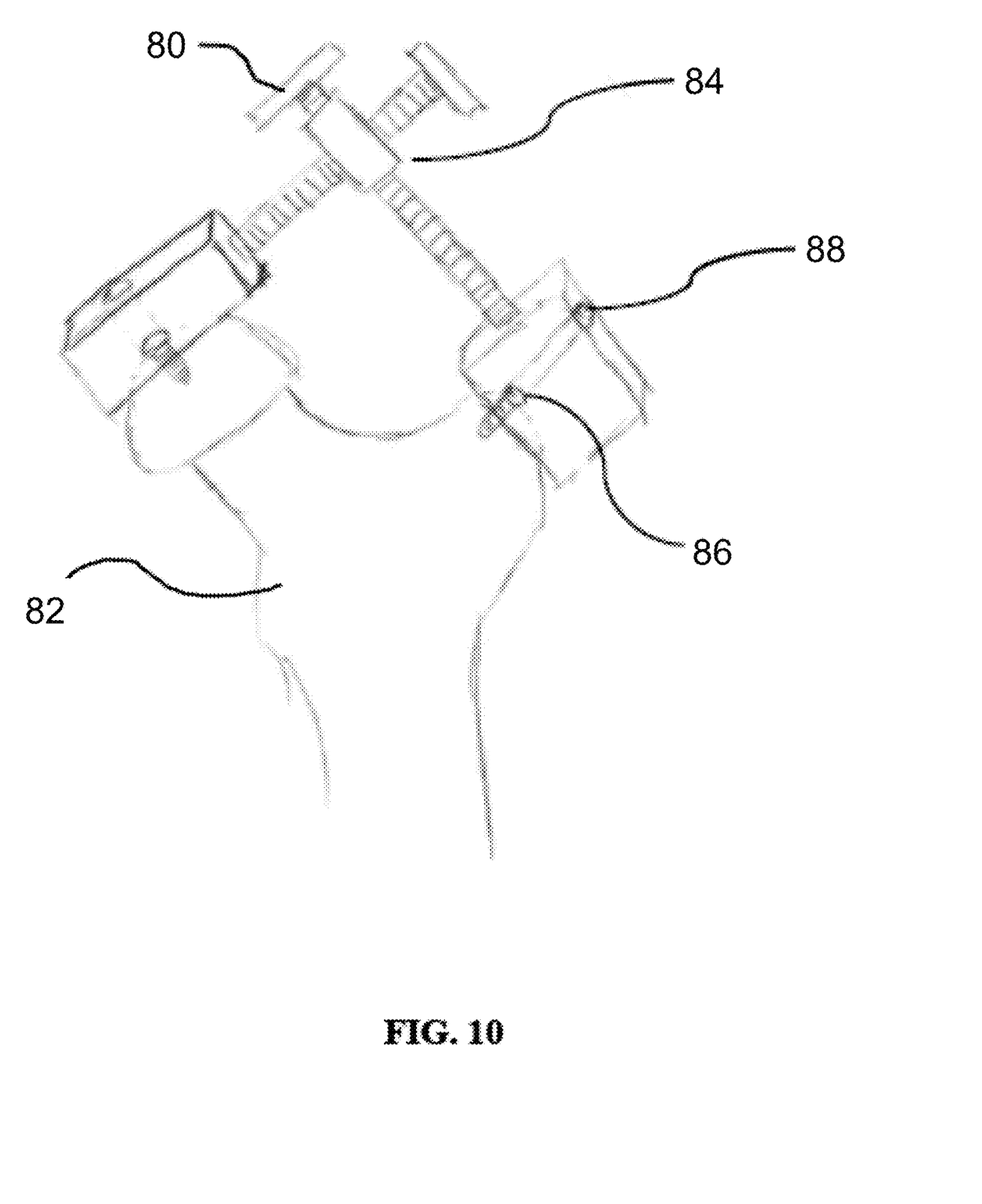
FIG. 10 is a perspective view of the proximal tibia with an embodiment of the adjustable registration jig in position on the bone.

FIG. 10 is a perspective view of the proximal tibia 82 with an embodiment of a generic adjustable registration jig 80 in position on the bone 82. The jig 80 can be adjusted using a mechanism 84. Once the jig 80 is placed on the bone 82, fiducial markers 86 can be placed into the bone 82 through an opening shown by reference numeral 88. Once the fiducial markers 86 have been placed in the bone 82, the registration jig 80 may be removed prior to bone cutting.

As a person skilled in the art will recognize from the previous detailed description and from the figures and claims, modifications and changes can be made to the preferred embodiments of the invention without departing from the scope of this invention defined in the following claims.

The invention claimed is:

1. A process for creating a curved contour on or within a patient's bone comprising:
   positioning a bone of a patient in a fixed position in a coordinate system;
   generating scan data of the bone;
   creating a three-dimensional surface model of the bone based on said scan data;
   generating a cutting program to modify a surface of the bone based on said three-dimensional surface model and a prosthesis having a bone interface shape that is complementary to the curved contour; and
   modifying the bone with one or more curved drill bits that is robotically driven and positioned based on said cutting program to form the curved contour, each of said one or more curved drill bits having a rotatory head extending from a nonlinear shaft and rotating within a nonlinear sheath.

2. The process of claim 1 further comprising immobilizing the patient and positioning the patient's bone for cutting with using at least one of a fiducial marker or a jig to determine a location and/or orientation of the patient's bone.

3. The process of claim 2 further comprising providing a unique mating between a registration guide and the patient's bone.

4. The process of claim 1 further comprising providing a unique mating between a registration guide and the patient's bone.

5. The process of claim 1 wherein modifying the bone is a plurality of sequential curved trajectories to remove sequential layers of the patient's bone.

6. A system for creation of a curved congruent contour on or within a patient's bone comprising:
   a processor configured to receive a set of scan data of the patient's bone and to generate a three-dimensional model and a cutting program to modify the surface of the patient bone based on the three-dimensional surface model and a prosthesis having a bone interface shape complementary to the curved contour; and
   a machine controlled by said processor and where said machine is mechanically coupled to at least one curved blade or curved drill bit, said curved blade or curved drill bit characterized by having a curved or nonlinear shaft and a rotatory head extending from the curved or nonlinear shaft and rotating within a nonlinear sheath, and wherein said machine robotically driven and positioned based on said cutting program to modify the patient's bone to form the curved contour.

7. The system of claim 6 wherein said machine is configured to remove bone material from the patient's bone in thin layers sequentially to achieve optimal bone preservation.

8. The system of claim 6 further comprising a fiducial marker configured to be adhered to the patient's bone or to the patient proximal to the bone.

9. The system of claim 8 further comprising a digitizer that intraoperatively determines a location of said fiducial marker.

10. The system of claim 6 wherein said scan data comprises at least one of computed tomography (CT), magnetic resonance imaging (MRI), or X-ray data.

11. The system of claim 6 further comprising an adjustable jig configured with three or more fiducial markers; and
    wherein said adjustable jig is adapted for placement on the patient's bone to determine a spatial orientation of the patient's bone in three-dimensions.

12. The system of claim 11 wherein said adjustable jig is made of at least one of a polymer, ceramic, metal, or prefabricated via a 3D printing processes.

13. A system for creation of a curved congruent contour on or within a patient's bone comprising:
    a processor configured to receive a set of scan data of the patient's bone and to generate a three-dimensional model and a cutting program to modify the surface of the patient bone based on the three-dimensional surface model and a prosthesis having a bone interface shape complementary to the curved contour;
    a machine controlled by said processor and where said machine is mechanically coupled to at least one curved blade or curved drill bit, said curved blade or curved drill bit characterized by having a curved shaft, and wherein said machine robotically driven and positioned based on said cutting program to modify the patient's bone to form the curved contour;
    a fiducial marker configured to be adhered to the patient's bone or to the patient proximal to the bone;
    a digitizer that intraoperatively determines a location of said fiducial marker; and
    a registration guide configured to fit to the patient bone, where said processor is configured to determine the registration guide location with respect to the fiducial markers locations and to determine the patient's bone location with respect to the registration guide.

14. The system of claim 13 wherein said registration guide is formed with a malleable registration guide blank, said malleable registration guide blank configured to couple to an adjustable model; and
    wherein said adjustable model is based on said three-dimensional model generated with said scan data.

* * * * *